US00PP20773P3

(12) United States Plant Patent
Hall et al.

(10) Patent No.: US PP20,773 P3
(45) Date of Patent: Feb. 23, 2010

(54) RASPBERRY PLANT NAMED 'ADELE'

(50) Latin Name: ***Rubus idaeus* L.**
Varietal Denomination: Adele

(75) Inventors: Harvey K. Hall, Motueka (NZ); Joseph Stephens, Auckland (NZ)

(73) Assignee: The New Zealand Institute for Plant and Food Research Limited, Auckland (NZ)

( * ) Notice: Subject to any disclaimer, the term of this patent is extended or adjusted under 35 U.S.C. 154(b) by 0 days.

(21) Appl. No.: 12/214,355

(22) Filed: Jun. 18, 2008

(65) Prior Publication Data

US 2008/0320622 P1 Dec. 25, 2008

Related U.S. Application Data

(60) Provisional application No. 60/936,282, filed on Jun. 19, 2007.

(51) Int. Cl.
*A01H 5/00* (2006.01)

(52) U.S. Cl. ..... Plt./204

(58) Field of Classification Search ..... Plt./204
See application file for complete search history.

*Primary Examiner*—Susan B McCormick Ewoldt
(74) *Attorney, Agent, or Firm*—Greenlee Winner and Sullivan PC

(57) ABSTRACT

A new and distinct floricane fruiting red raspberry, *Rubus idaeus* L., variety is described. The variety results from selection among a population of seedlings derived from controlled pollination crossing of the raspberry varieties known as 'Chilcotin' (not patented) and an unreleased selection with the breeder code 86107O58 (not patented). The fruit of this new variety has an attractive appearance characterized by very shiny, mid light-red fruit color. The new variety is distinguished from others by its high yields of firm and attractive conical shaped, uniform sized, large, red berries that ripen in the mid season. The plant exhibits a semi spine-free upright growth habit, of strong vigor. The new variety appears suitable for the fresh fruit market and has been named 'Adele'.

4 Drawing Sheets

Genus and species of plant claimed: *Rubus idaeus* L.
Variety denomination: Adele

CROSS-REFERENCE TO RELATED APPLICATION

This application claims the benefit of U.S. provisional application Ser. No. 60/936,282 filed Jun. 19, 2007.

BACKGROUND TO THE INVENTION

The new variety of red raspberry, *Rubus idaeus* L., was created in the course of a planned breeding program carried out at Nelson, Motueka, New Zealand. The parents used to make the cross in 1990, were the varieties 'Chilcotin' (seed parent) and selection 86107O58 (pollen parent).

Seed from this cross was grown and the original plant of the new variety was selected during the 1993–94 summer (Southern Hemisphere) and was found to exhibit:

(a) a semi spine-free upright growth habit of strong vigor,
(b) the ability to form attractive very shiny red fruit of good flavor in high yields on medium length fruiting laterals that ripen mid season, and
(c) resistance to Raspberry Bushy Dwarf Virus (RBDV).

The new variety was first asexually propagated in 1998, at Motueka, Nelson, New Zealand, being reproduced by vegetative cuttings arising from root cuttings. Cuttings developed this way in spring, root within a 3–4 week propagation period, and thus plants suitable for field planting are then ready in autumn of the same year. The resulting plants propagated true to type, demonstrating that the characteristics of the new cultivar are stable and are transmitted without change through succeeding generations. Since 2000, 'Adele' has been asexually propagated in vitro via tissue culture methods. The cultivar has propagated true to type via these means.

SUMMARY OF THE INVENTION

The new variety was selected from a population of seedlings derived from crossing the raspberry varieties known as 'Chilcotin' (not patented) and an unreleased selection with the breeder code 86107O58 (not patented). The new variety was assigned the breeder code, 90312CF0 (subsequently coded HR119at the advanced selection stage). The new variety has since been named 'Adele'.

The new variety was tested and evaluated during the years 1996 to 2005 in the Nelson Region, New Zealand (41.10° S., 172.97° E).

When compared to the parent 'Chilcotin', the new variety was found to have larger, more conical shaped fruit of similar color but in higher yields. 'Adele' is further distinguished from 'Chilcotin' by having canes that have fewer spines.

When compared to the parent 86107O58, the new cultivar exhibits fruit that are brighter red in color, larger and easier to remove from the bush. 'Adele' also has more spines than 86107O58 which was spineless.

Berries of the new variety are suitable for hand picking and consumption as mid season, high-grade fresh fruit.

BRIEF DESCRIPTION OF THE DRAWINGS

The accompanying photographs show typical specimens of the plant, foliage and fruit of the new variety as depicted in colors as nearly true as is reasonably possible to make the same in a color illustration of this character.

The photographs were taken on mature plants in Nelson Region in New Zealand and Washington State, United States of America (U.S.A.).

DETAILED DESCRIPTION

Figure 1:
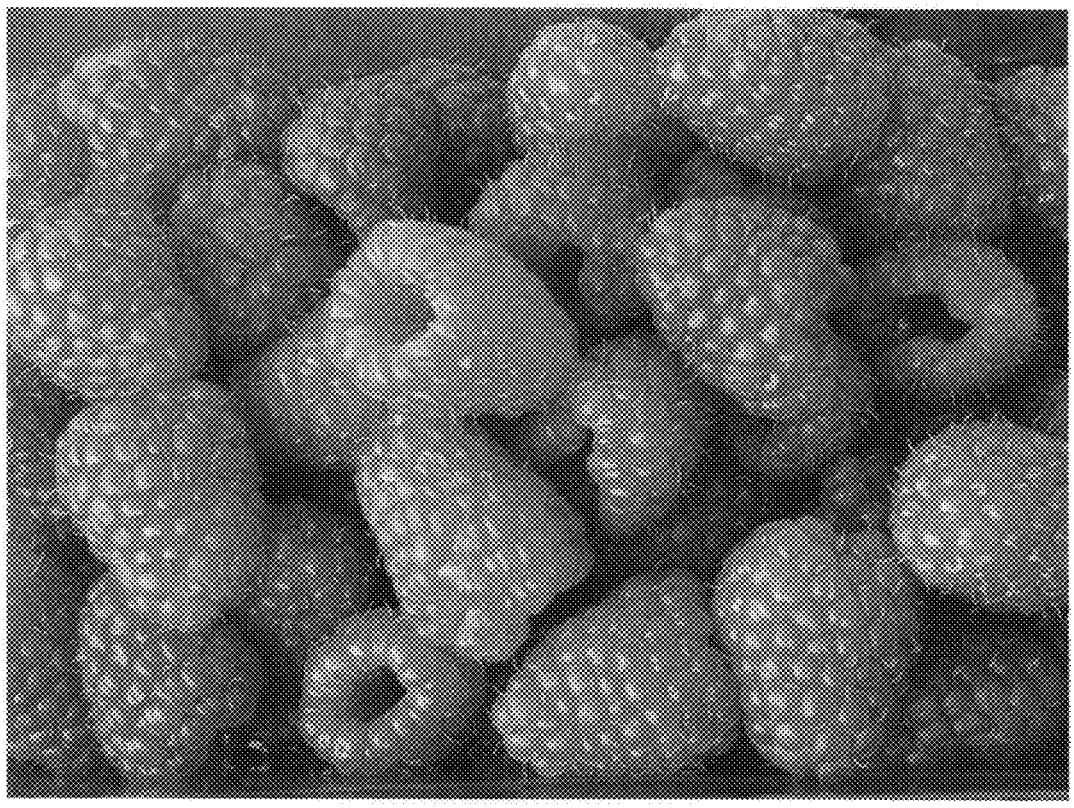
FIG. 1 shows close-up views of typical fruit of the variety 'Adele'.

Horticultural terminology is used in accordance with UPOV guidelines for raspberry. All dimensions in millimeters, weights in grams (unless otherwise stated). Where a color reference is given these refer to the R.H.S. Colour Chart, The Royal Horticultural Society, London. 4th Edition, 2001. The specimens described were grown at HortResearch Nelson, New Zealand and in Washington State, U.S.A.

Environmental data for the New Zealand growing area demonstrates conditions in spring and early summer (equating to the harvest period for the variety) as follows:

Spring (September/October); mean daily temperature in the range 10–12° C. (mean daily minimum 5.8° C., mean daily maximum 16.5° C.).

Early summer (December/January); mean daily temperature 16.8° C. (mean daily minimum 11.1° C., mean daily maximum 22.4° C.).

A cool temperate area, frost conditions are typically experienced in winter, with the lowest winter air temperature unlikely to be colder than −6° C. Average annual rainfall is approximately 1125mm.

Figure 2:
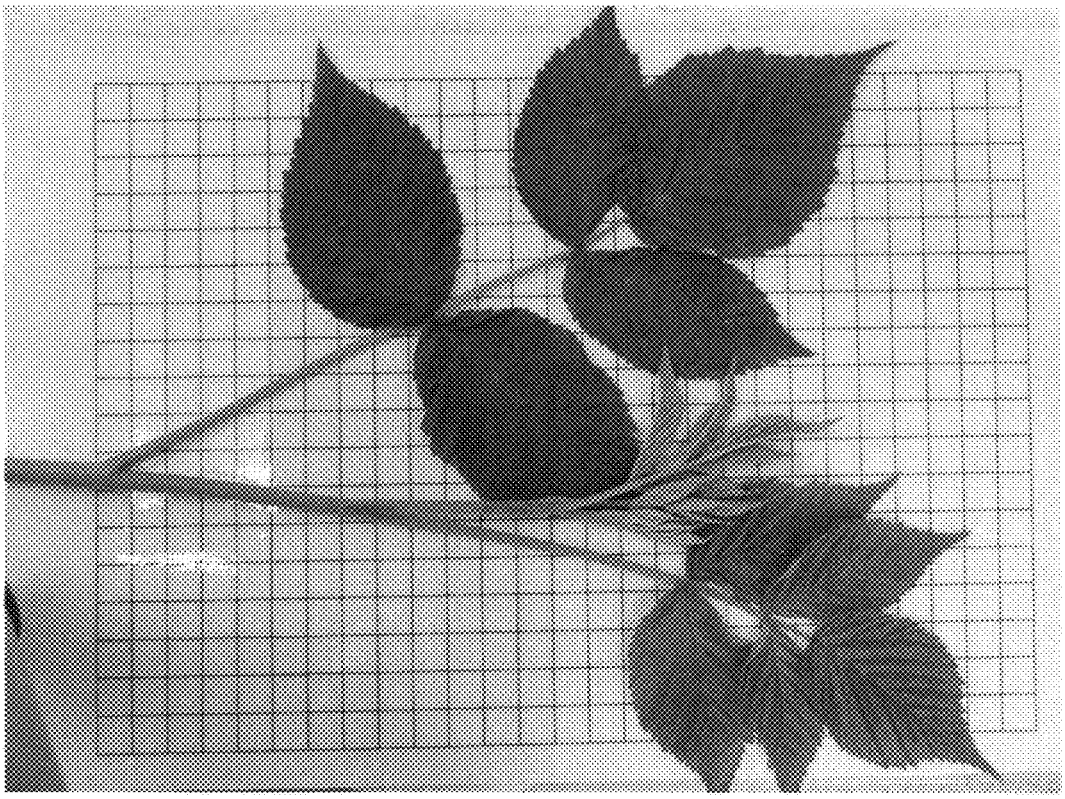
FIG. 2 shows the leaf and shoot tip of a fruiting lateral of the variety 'Adele'.
Figure 3:
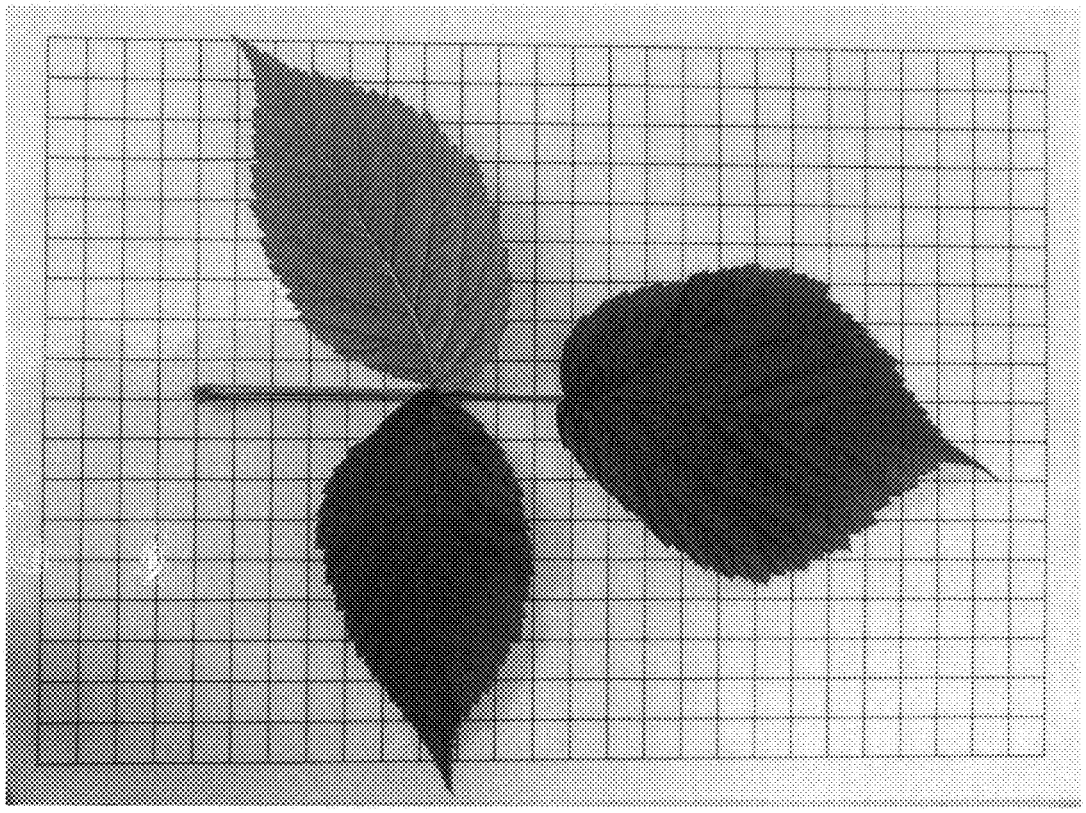
FIG. 3 shows a floricane leaf of the variety 'Adele'; view is of the upper and lower surfaces.
Figure 4:
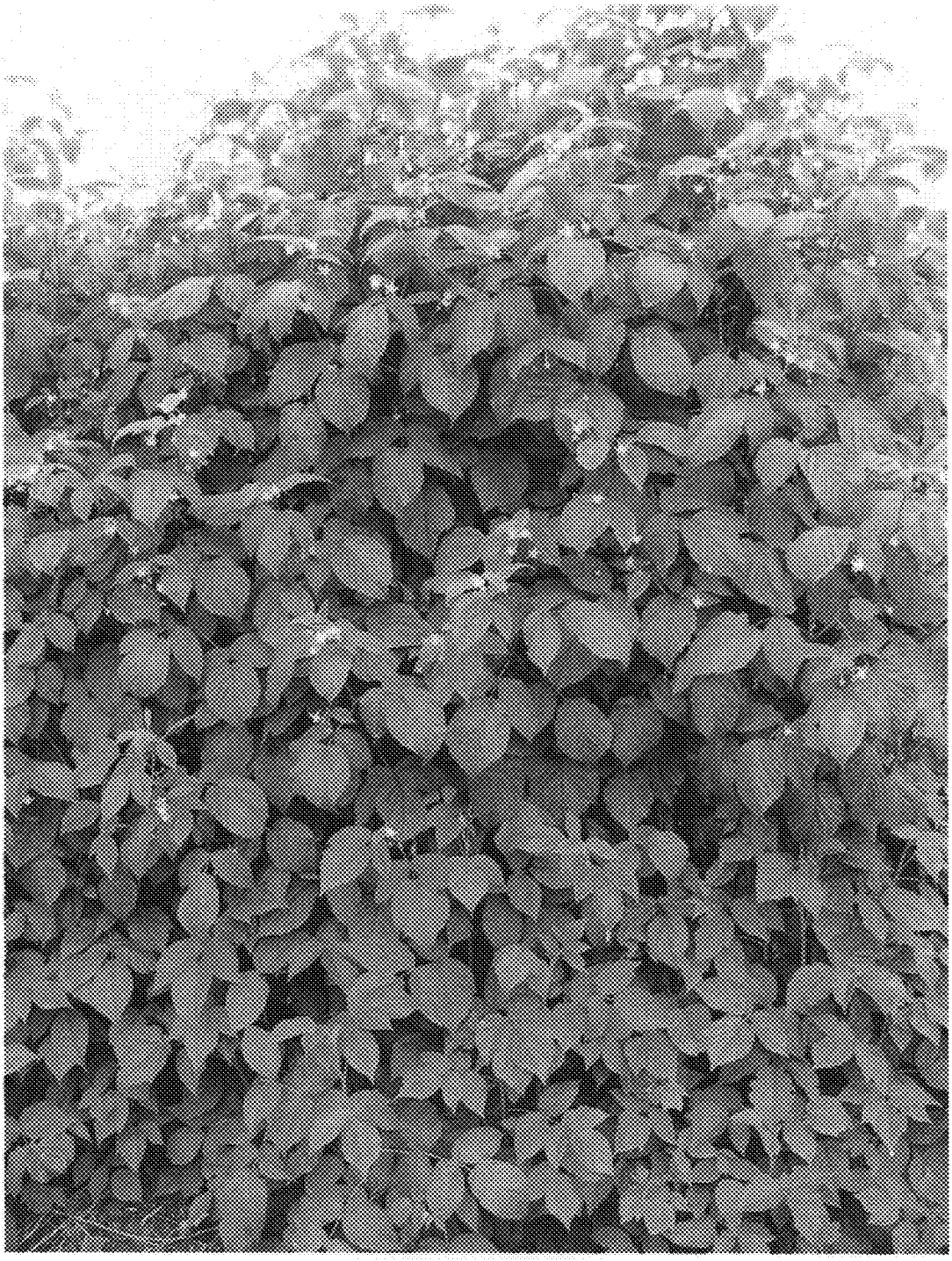
FIG. 4 shows typical plants of the variety 'Adele' showing the upright nature of the canes at full canopy development.

Plant and foliage: The plant exhibits an upright growth habit (FIG. 4). Mature plant height is commonly in the range 2000 mm to 2500 mm, although this may vary with the growing conditions. Strong vigor is exhibited and internode length is typically in the range 80–90 mm. Plants have many young shoots; canes have few spines. Spines (prickles/thorns) are sparse, particularly on the upper cane section and are small on mature canes (typically approximately 0.7mm long), but may be denser and longer on juvenile canes. Spine color is light red with little anthocyanin coloration. Plants of 'Adele' have been observed to be more spiny compared with some other commercial varieties, for instance, 'Glen Ample' (not patented) which have no spines, although less spiny than those of 'Marcy' (not patented) which are very spiny. Canes are pubescent indicating the presence of gene H. Canes typically show light brown-tan coloration (near Greyed-orange 165A) in winter. During the growing season some purple coloration (near Red-purple 59A) is evident on the sun-exposed side of the cane. Young shoots are erect and are near Yellow-green 144C in color. The leaves are compound, moderately crinkled, flat and moderately dull, with strong silver coloration on the leaf underside (FIGS. 2 and 3). The number of primocane leaflets per internode is both three and five. The base of the terminal leaflet is concave in shape and typically average 80–90 mm in diameter and 100–110mm in length. The coloration of the upper surface of the leaf is green (near Yellow-green 146A), the under side being markedly lighter in coloration (near Greyed-green 191A). While the leaves do not have distinguished marginal or vein coloration, the venation has noticeable rises and falls, and the leaf margin is typically serrate. The leaf petiole typically averages approximately 100 mm in length and 3 mm in diameter. It is near Yellow-green 144B in color. The fruit is borne entirely on the previous year's growth. Fruiting laterals are medium long in length, commonly measuring 500–700 mm, and are weakly ascending and horizontal when fruit has ripened. Fruit presentation at harvest time is excellent and well suited to hand-picking.

Infloresence: White flowers are borne on short slender pedicels that have few spines (thorns/prickles). At Nelson, New Zealand the date bud burst commences is approximately 8 September, with fifty percent of buds burst by mid-late September (approximately 22 September). The time of bloom is mid season for a summer-fruiting raspberry, with peak flowering around mid November. Flowers are numerous and borne on a paniculate inflorescence. Typically there are five petals, elongated ovate in shape with a rounded apex and flat base. The petals average approximately 7.4 mm in length and 4.1 mm in width. They are typically smooth in texture, have a smooth margin and are near White 155C in color. The pedicel length averages approximately 34.0 mm long. However, the more basal the pedicel the longer it commonly becomes with pedicel lengths up to about 70 mm being observed. The pedicel averages approximately 1.0 mm in diameter and is near Yellow-green N144A in color and has weak anthocyanin coloration on the sun-exposed side. A typical king flower diameter averages approximately 26 mm (from sepal tip to sepal tip i.e. the widest part of the flower). The flowers are predominantly borne singly, although sometimes in clusters of two or more. Terminal branch flower clusters frequently consist of two flowers and basal flower clusters may number three to five. The flowers have no discernible fragrance. Five sepals are present. These are green in coloration (near Yellow-green 144A on the bottom and near Green 138C on top) and measure approximately 12–13 mm in length from base to tip. The reproductive organs are typical for flowers of *Rubus idaeus* L.; the stigmas average approximately 105 in number and are near Yellow-green 145C in color; there are approximately 80–90 stamens the filaments of which are near White 155C in color and average 4.4 mm in length. Anthers are brown and (depending on maturity) near Brown 200D in color.

Harvest: Fruit commences ripening in early December in New Zealand. The typical start date for picking the new cultivar is 13 December. Fifty percent of the harvest is typically completed by 28 December, and the main harvest period is complete by mid January (approximately 18 January). The time of fruit ripening has been observed to occur before that in New Zealand for 'Tulameen' (not patented).

'Adele' is not suitable for harvest by machine due to the moderately strong force required to dislodge the berry from the receptacle. 'Adele' is recommended for mid season production for fresh market fruit. The variety may also be suited to long cane production systems due to its high quality fruit and suitability to fresh market production.

Fruit: Fruit is produced on previous year's cane in summer. Berry size is medium large. The average berry weight is approximately 4.5g; individual fruit ranging between 4–6g in weight. Fruit size is uniformly large through the harvest maturity period. Fruit shape is typically ovate-conical; on the basis of fruit length to width ratio, fruit is longer than broad. On average berries are 25–30 mm long and 15–20 mm wide at the widest point. Fruit color is light mid-red;

external color near Red-46A, internal color near Red 46A. There are few hairs present on the fruit skin resulting in high glossiness. High fruit glossiness is a distinct feature of this cultivar. The fruit skin is characteristically very shiny, more so than fruit from the variety 'Skeena' (not patented) which appear moderately dull by comparison. Drupelets number typically 100–105 and are quite large, typically 4.4 mm in diameter. Fruit have a medium firm and fleshy texture with good raspberry flavor. The seeds average 3.0 mm long and 1.5 mm wide, and are near Orange 27A in color when dry. Seed numbers per fruit average 100–105 and weigh on average 0.2g per fruit (or on average individually 1.9mg). 'Adele' fruit has been observed to have a good shelf life in Nelson Region, New Zealand. Fruit shelf life appears improved over the commercial varieties 'Marcy' (not patented) and 'Skeena' (not patented), and comparable to fruit from the variety 'Tulameen' (not patented). Yield is high, typically in the range 14–18 T/ha equivalent.

Plant and disease resistance: The plant does not seem to be susceptible to yellow rust (*Phragmidium rubi-idaei*,) and appears resistant to Raspberry Bushy Dwarf Virus (RBDV).

Since the selection of this clone in 1993–94 numerous tests for RBDV have been carried out on 'Adele' in New Zealand using ELISA, but on no occasion has the virus been detected in spite of high infection pressure. From this we suggest that 'Adele' is likely to be resistant to the common strain of RBDV found in New Zealand. Resistance to aphids is unknown.

Geographical adaptation: Observations indicate that the variety is well-suited to production in regions that offer a medium amount of winter chill, for example, 'Adele' performs well in the cool temperate climate of the Nelson region, New Zealand, under standard management practices for commercial raspberry production. Initial indications are that 'Adele' also performs well in USDA Plant Hardiness zones 8–10 (published as the 2003 US National Arboretum "Web Version" of the USDA Plant Hardiness Zone Map USDA Miscellaneous Publication No.1475, Issued January 1990).

We claim:

1. A new and distinct raspberry plant as herein illustrated and described.

* * * * *